(12) United States Patent
Guez

(10) Patent No.: US 8,754,388 B2
(45) Date of Patent: Jun. 17, 2014

(54) RADIATION CONTROL AND MINIMIZATION SYSTEM AND METHOD USING COLLIMATION/FILTERING

(71) Applicant: ControlRad Systems, Inc., Radnor, PA (US)

(72) Inventor: Allon Guez, Narberth, PA (US)

(73) Assignee: ControlRad Systems, Inc., Penn Valley, PA (US)

( * ) Notice: Subject to any disclaimer, the term of this patent is extended or adjusted under 35 U.S.C. 154(b) by 0 days.

(21) Appl. No.: 13/856,429

(22) Filed: Apr. 3, 2013

(65) Prior Publication Data

US 2013/0301797 A1 Nov. 14, 2013

Related U.S. Application Data

(63) Continuation of application No. 13/311,486, filed on Dec. 5, 2011, now Pat. No. 8,445,878.

(60) Provisional application No. 61/453,540, filed on Mar. 16, 2011.

(51) Int. Cl.
*A61N 5/10* (2006.01)
*A61N 5/00* (2006.01)
*G21K 1/02* (2006.01)

(52) U.S. Cl.
USPC ............... 250/505.1; 250/492.1; 250/492.3; 250/396 R; 378/16; 378/19; 378/65; 378/145; 378/147

(58) Field of Classification Search
USPC ....... 250/505.1, 492.1, 492.3, 396 R; 378/16, 378/19, 65, 145, 147
See application file for complete search history.

(56) References Cited

U.S. PATENT DOCUMENTS

| | | | |
|---|---|---|---|
| 5,010,562 A | 4/1991 | Hernandez et al. | |
| 5,091,926 A | 2/1992 | Horton et al. | |
| 5,094,522 A | 3/1992 | Sourdille et al. | |
| 5,206,894 A | 4/1993 | Makrinos et al. | |
| 5,558,619 A | 9/1996 | Kami et al. | |

(Continued)

FOREIGN PATENT DOCUMENTS

| | | |
|---|---|---|
| EP | 1 374 774 | 8/2008 |
| JP | 2002-136507 | 5/2002 |

(Continued)

OTHER PUBLICATIONS

Miller DL, Batter S, Schueler BA, Wagner LK, Strauss KJ, Vano E.: "Clinical radiation management for fluoroscopically guided interventional procedures." Radiology. Nov. 2010;257(2):321-332 (12 pgs).

(Continued)

*Primary Examiner* — Nikita Wells
(74) *Attorney, Agent, or Firm* — Goodwin Procter LLP

(57) ABSTRACT

A radiation control system and method are provided in which radiation delivered to a patient and/or the operator of the equipment is minimized. The radiation control system may be used in a large variety of applications including applications in which radiation source is used to inspect an object, such as, for example, medical imaging, diagnosis and therapy, in manufacturing operation using radiation, in airports scanning systems, in different security setups, and in nuclear reactors automation and process control. The radiation control system and method may also be used with 3D imaging.

15 Claims, 11 Drawing Sheets

(56) References Cited

U.S. PATENT DOCUMENTS

| | | | |
|---|---|---|---|
| 5,583,795 | A | 12/1996 | Smyth |
| 5,850,211 | A | 12/1998 | Tognazzini |
| 5,911,036 | A | 6/1999 | Wright et al. |
| 5,926,264 | A | 7/1999 | Beale et al. |
| 6,111,934 | A | 8/2000 | Foerst et al. |
| 6,175,610 | B1 | 1/2001 | Peter |
| 6,215,850 | B1 | 4/2001 | Blake et al. |
| 6,241,670 | B1 | 6/2001 | Nambu |
| 6,368,269 | B1 | 4/2002 | Lane |
| 6,608,884 | B1 | 8/2003 | Mazess |
| 6,785,358 | B2 | 8/2004 | Johnson et al. |
| 6,847,336 | B1 | 1/2005 | Lemelson et al. |
| 6,886,137 | B2 | 4/2005 | Peck et al. |
| 7,016,469 | B2 | 3/2006 | Johnson et al. |
| 7,116,752 | B2 | 10/2006 | Takahashi et al. |
| 7,257,194 | B2 | 8/2007 | Smith |
| 7,283,615 | B2 | 10/2007 | Morehead |
| 7,331,929 | B2 | 2/2008 | Morita et al. |
| 7,396,129 | B2 | 7/2008 | Endrikhovski et al. |
| 7,403,597 | B2 | 7/2008 | Raupach |
| 7,436,928 | B2 | 10/2008 | Urano et al. |
| 7,460,940 | B2 | 12/2008 | Larsson et al. |
| 7,778,390 | B2 | 8/2010 | Schliermann |
| 7,783,007 | B2 | 8/2010 | Echner |
| 7,809,111 | B2 | 10/2010 | Meer et al. |
| 7,835,498 | B2 | 11/2010 | Bonfiglio et al. |
| 7,851,736 | B2 | 12/2010 | Spahn |
| 7,869,571 | B2 | 1/2011 | Hsieh et al. |
| 7,983,391 | B2 | 7/2011 | Machan et al. |
| 8,085,902 | B2 | 12/2011 | Bonfiglio et al. |
| 8,130,904 | B2 | 3/2012 | Bowers et al. |
| 8,445,878 | B2 * | 5/2013 | Guez .................... 250/505.1 |
| 2004/0212712 | A1 | 10/2004 | Stavely et al. |
| 2004/0242988 | A1 | 12/2004 | Niwa et al. |
| 2007/0121065 | A1 | 5/2007 | Cox et al. |
| 2008/0253519 | A1 | 10/2008 | Bonfiglio et al. |
| 2009/0154650 | A1 | 6/2009 | Tanabe |
| 2009/0161827 | A1 | 6/2009 | Gertner et al. |
| 2010/0074392 | A1 | 3/2010 | Behling et al. |
| 2010/0204608 | A1 | 8/2010 | Sugio et al. |
| 2010/0225746 | A1 | 9/2010 | Shpunt et al. |
| 2010/0237259 | A1 | 9/2010 | Wang |
| 2011/0013742 | A1 | 1/2011 | Zaiki et al. |
| 2011/0060423 | A1 | 3/2011 | Bonfiglio et al. |
| 2011/0075805 | A1 | 3/2011 | Machan et al. |
| 2012/0057674 | A1 * | 3/2012 | Zhang ........................ 378/62 |
| 2012/0235064 | A1 | 9/2012 | Guez |
| 2012/0235065 | A1 | 9/2012 | Guez |
| 2012/0236996 | A1 * | 9/2012 | Guez et al. ................ 378/117 |
| 2013/0129043 | A1 * | 5/2013 | Morton et al. ............. 378/62 |

FOREIGN PATENT DOCUMENTS

| | | |
|---|---|---|
| JP | 2004-275792 | 10/2004 |
| JP | 2005-296277 | 10/2005 |
| JP | 2006-271722 | 10/2006 |
| JP | 2007-310228 | 11/2007 |
| JP | 2009-160467 | 7/2009 |
| JP | 2010-264310 | 11/2010 |
| JP | 2010-284325 | 12/2010 |

OTHER PUBLICATIONS

FDA. White Paper: Initiative to Reduce Unnecessary Radiation Exposure from Medical Imaging. In: Administration CfDaRHUSFaD, ed. 2010 (12 pgs).

Arthur WR, Dhawan J, Norell MS, Hunter AJ, Clark AL: :Does cardiologist—or radiographer-operated fluoroscopy and image acquisition influence optimization of patient radiation exposure during routine coronary angiography?Br J Radio!. Sep. 2002;75(897):748-753 (6 pgs).

Mavrikou I, Kottou S, Tsapaki V, Neofotistou V. "High patient doses in interventional cardiology due to physicians' negligence: how can they be prevented?" Radiat Prot Dosimetry. 2008;129(1-3):67-70 (4 pgs).

Article: State of Illinois, Illinois Emergency Management Agency, Info: Everyday uses of Radiation & Radioactive Materials (2 pgs), Sep. 2005.

Xu, T., et al., "Patent-specific Region-of-Interest Fluoroscopy Device for X-ray Dose Reduction," Radiology, Feb. 2004, vol. 226, No. 2, pp. 585-592 (8 pgs).

Rudin, et al., "Clinical Application of Region-of-Interest Techniques to Radiologic Imaging," Imaging & Therapeutic Technology, vol. 16, No. 4, Jul. 1996, pp. 895-902 (8 pgs).

Charlier, et al., "Eye-Controlled Microscope for Surgical Applications," Sourdille Ph (ed.): Evolution of Microsurgery. Dev. Ophthalmol. Basel, Karger, 1991, vol. 22, pp. 154-158 (5 pgs).

J.A. Rowlands, N. Robert, Order of Magnitude Reduction of Radiation Exposure in Fluoroscopically Guided Interventional Procedures, Medical Physics, vol. 38, No. 6, Jun. 2011, p. 3457 (1 pg).

Reingold, et al., "Gaze-Contingent Multiresolutional Displays: An Integrative Review," Human Factors: The Journal of the Human Factors and Ergonomics Society Summer 2003 vol. 45 No. 2 307-328 (22 pgs.).

Reingold, et al., "Eye movements and visual expertise in chess and medicine," In: SP Liversedge ID, Gilchrist S, Evening, editors. Oxford Handbook on Eye Movements. Oxford, UK: Oxford University Press (28 pgs), 2011.

Vasan, et al., "Spatially Different, Real-Time Temporal Filtering and Dose Reduction for Dynamic Image Guidance during Neurovascular Interventions," 33rd Annual International Conference of the IEEE EMBS, Boston, MA, Aug. 30-Sep. 3, 2011, pp. 6192-6195 (4 pgs).

* cited by examiner

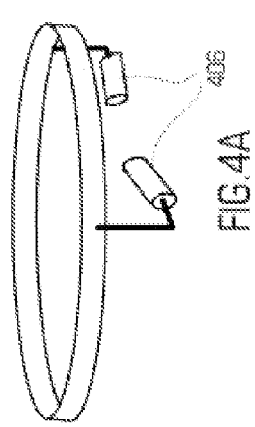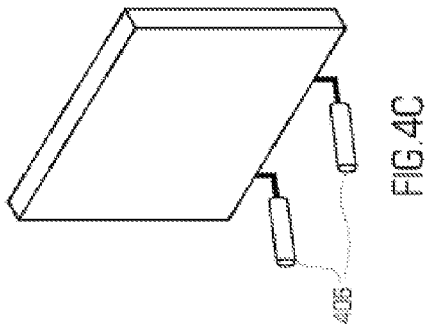

RADIATION CONTROL AND MINIMIZATION SYSTEM AND METHOD USING COLLIMATION/FILTERING

PRIORITY CLAIMS/RELATED APPLICATIONS

This application is a continuation of and claims priority under 35 USC 120 to U.S. patent application Ser. No. 13/311,486, filed on Dec. 5, 2011 and entitled "Radiation Control And Minimization System And Method Using Collimation/Filtering" which in turn claims the benefit under 35 USC 119(e) to U.S. Provisional Patent Application Ser. No. 61/453,540 filed on Mar. 16, 2011 and entitled "Radiation Control and Minimization System and Method", the entirety of both of which are incorporated herein by reference.

FIELD

The disclosure relates generally to radiation systems (whether for industrial, security, therapeutic use or imaging) and in particular to systems to minimize the radiation to which a patient, a person, an object or an operator is exposed.

BACKGROUND

Devices and system that generate various forms of radiation/ionizing energy are used for various therapeutic/treatment, diagnostic or imaging purposes. For example, various forms of radiation/ionizing energy may be used to inspect an object (such as in airports scanning systems, different security setups, manufacturing and process control) or inspect a patient (such as in a clinic or a hospital, e.g. Cath lab, where a surgeon/therapist operates an X Ray or CT system.)

The medical imaging industry for example is heavily focused on reducing the radiation dose in diagnostic and treatment procedure that include hardware and software modification and operator room procedures. See Miller D L, Balter S, Schueler B A, Wagner L K, Strauss K J, Vano E. "Clinical radiation management for fluoroscopically guided interventional procedures", Radiology. November 2010; 257 (2):321-332. The reporting of radiation dose is one of the QA measurements that are required by Medicare. Furthermore, the Food and Drug Administration in their 2010 "White paper" called for significant reduction of the "unnecessary radiation". FDA, "White Paper: Initiative to Reduce Unnecessary Radiation Exposure from Medical Imaging. In: Administration CfDaRHUSFaD, ed. 2010.

There are two main components that can reduce radiation exposure. The first component is the technical improvements of the x-ray equipment, such as investment in better filtering, collimators, acquisition equipment and image analysis. The other component is the way the operator uses the radiation, which includes the length of exposure, distance from the source to the patient and proper collimation. See Miller D L, Balter S, Schueler B A, Wagner L K, Strauss K J, Vano E. "Clinical radiation management for fluoroscopically guided interventional procedures", Radiology. November 2010; 257 (2):321-332 and Arthur W R, Dhawan J, Norell M S, Hunter A J, Clark A L, "Does cardiologist- or radiographer-operated fluoroscopy and image acquisition influence optimization of patient radiation exposure during routine coronary angiography?", Br J Radiol. September 2002;75(897):748-753. The radiation education of the operator/physician is critical to reduce the radiation dose and trained physician utilize significantly lower amounts of radiation. A similar focus to reduce radiation exposure exists in the non-medical areas. For example, the nuclear industry has been very sensitive for several decades to radiation exposure and in many other manufacturing fields there are strict guidelines for minimizing exposure. See Http://www.state.il.us/iema/publications/pdf/IEMA%20032%20Everyday%20Uses%20of%20Radiation.pdf.

For example, during a fluoroscopy guided, interventional medical procedure, there are periods of time when the operator (usually a physician), even when he/she activates the radiation source which radiates the patient and the staff does not receive the information that is generated by a radiation source. This radiation (and the information in it) are not only wasted but are furthermore needlessly damaging to the patient and the staff/operator of the radiation source. This may be referred to as "Unattended Radiation" (UR) which is undesirable. Thus, in the various different applications in which objects or patients are being inspected, it is desirable to reduce the Unattended Radiation and therefore minimize the exposure to the potentially harmful radiation by the operator and/or patient and it is to this end that the disclosure is directed.

BRIEF DESCRIPTION OF THE DRAWINGS

FIG. 4A-4C illustrates three examples of eye movement tracking attention monitoring devices;

DETAILED DESCRIPTION OF ONE OR MORE EMBODIMENTS

The disclosure is particularly applicable to a system used to inspect/treat/diagnose a patient in which the radiation is minimized and it is in this context that the disclosure will be described. It will be appreciated, however, that the system and method for reducing radiation exposure has greater utility since it can be used in any application in which it is desirable to minimize the radiation exposure of an object or a person, such as a patient or operator, that can be harmed by that exposure and those applications may include systems that inspect an object in which the operator may be exposed to unneeded radiation (such as airports scanning systems, different security setups, manufacturing and process controls, etc.) or system to inspect a patient (such as in a clinic or a hospital, e.g. Cath lab, where a surgeon/therapist operates an X Ray or CT system, a diagnostic procedure, a treatment procedure, an imaging procedure, etc.) The radiation minimization can be used with any type of radiation including ionizing radiation sources (x-ray, gamma, alpha and beta) and non-ionizing radiation sources (electromagnetic, US). The radiation minimization may also be used with 3D systems such as CT, MRI, Bi-Plane and others.

Figure 1:
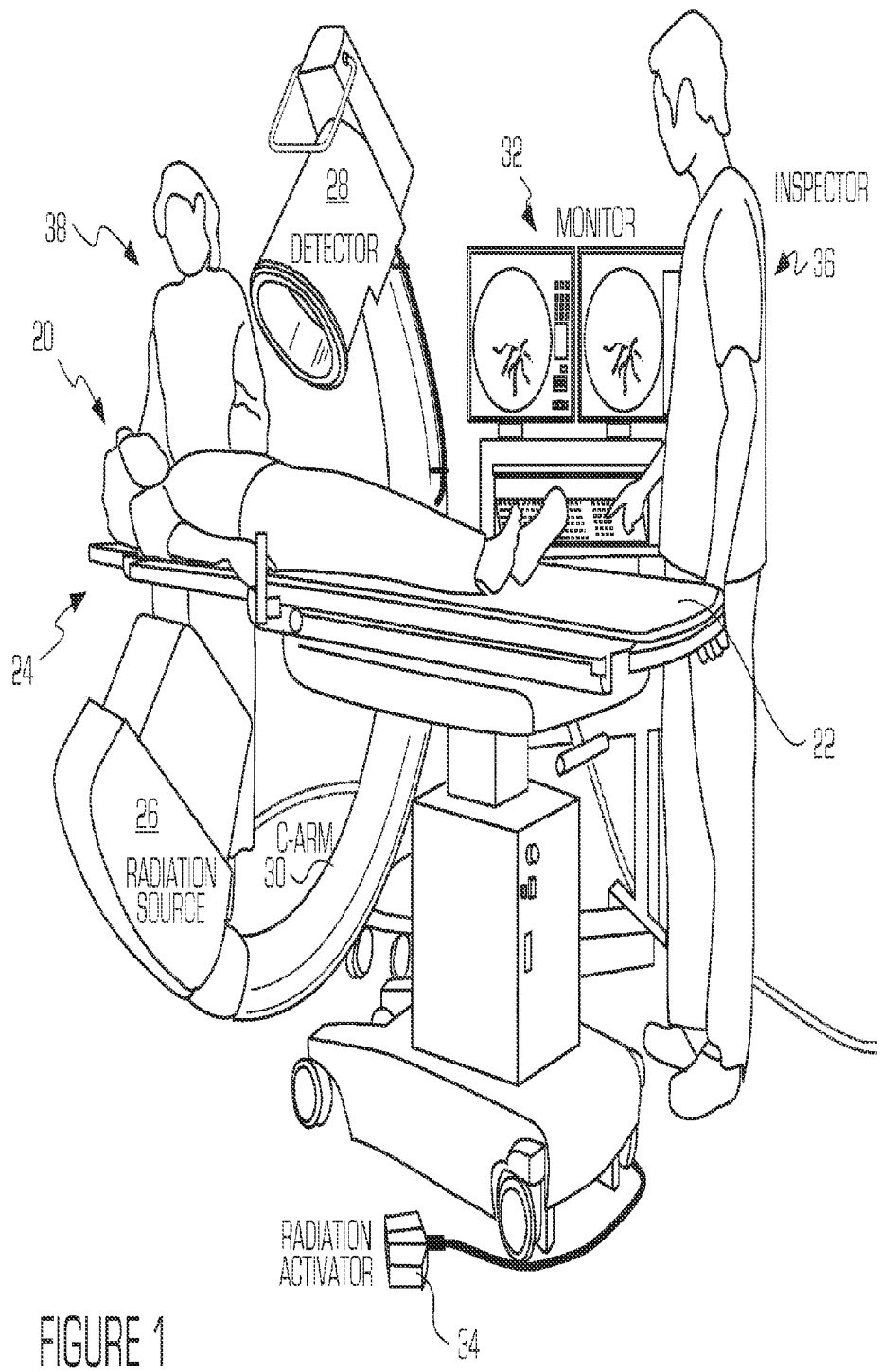
FIG. 1 illustrates an example of a medical application in which a radiation source is used to inspect a patient in which unattended radiation may occur.

FIG. 1 illustrates an example of a medical application in which a radiation source is used to inspect a patient in which unattended radiation may occur. In the medical application, a patient 20 may rest on a surface 22 of an apparatus 24. In this example, the apparatus in this example has a radiation source 26 and a detector 28 connected to each other by a C arm 30 wherein the radiation is directed at the patient 20 to image or treat a particular portion of the patient. The apparatus 24 may also include a monitor 32 on which the results of the imaging/treatment of the patient are displayed. The apparatus may also include a radiation activator 34 that allows an operate to activate the emission of radiation from the radiation source. In addition to the patient 20, there may also be an operator 36 (sometimes a physician) and an assistant 38 who are close to the apparatus 24. As a result, the patient, operator and the assistant may also be exposed to radiation and, more particularly, exposed to unattended radiation that is minimized by the radiation reduction and minimization system that is described below. The medical application shown in FIG. 1 is merely representative of the types of system that the radiation reduction and minimization system may be used for since the radiation reduction and minimization system may be used for any system in which it is desirable to be able to reduce/minimize unattended radiation, such as, but not limited to the systems identified above.

Figure 2:
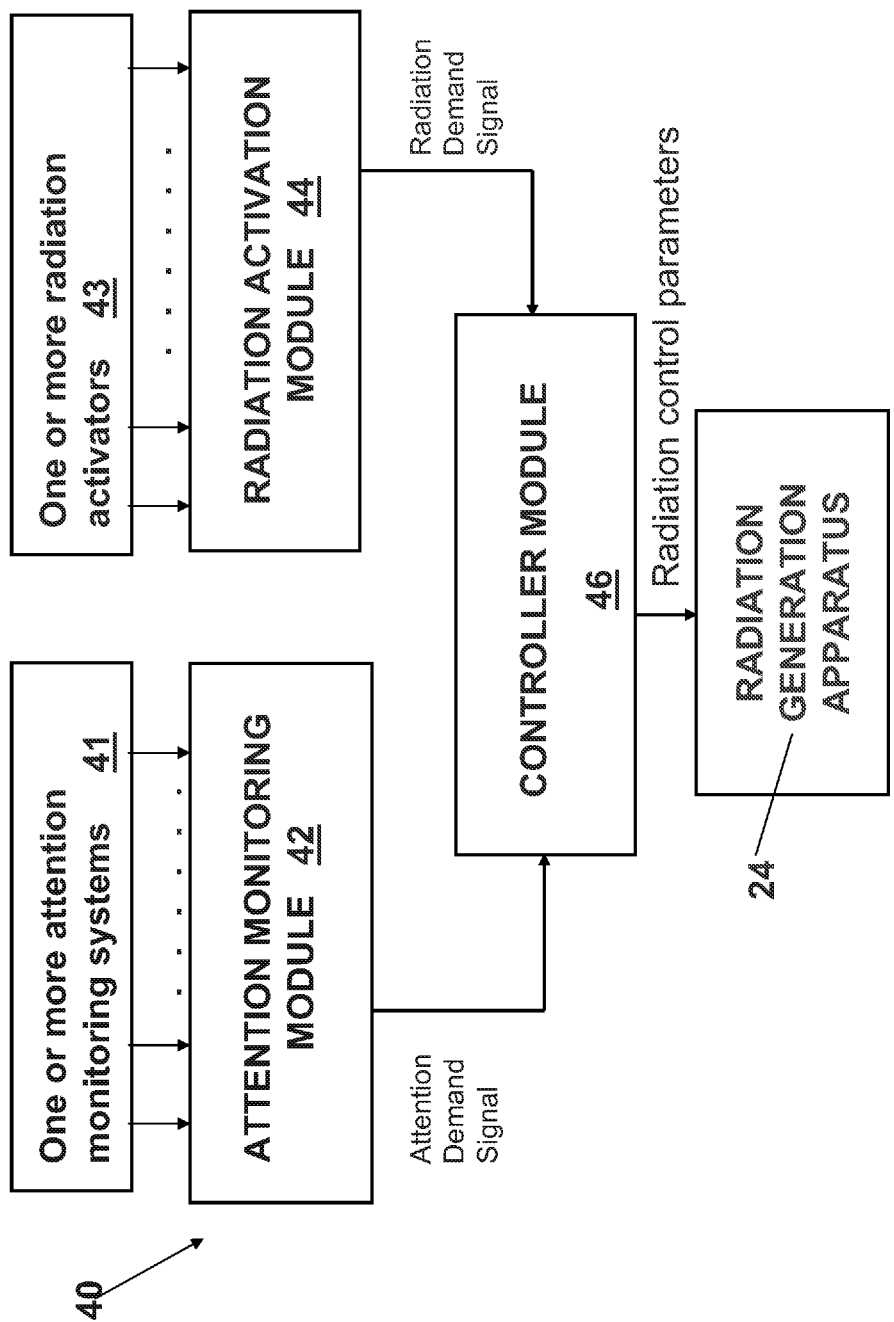
FIG. 2 illustrates an embodiment of a radiation reduction and minimization apparatus.
Figure 3:
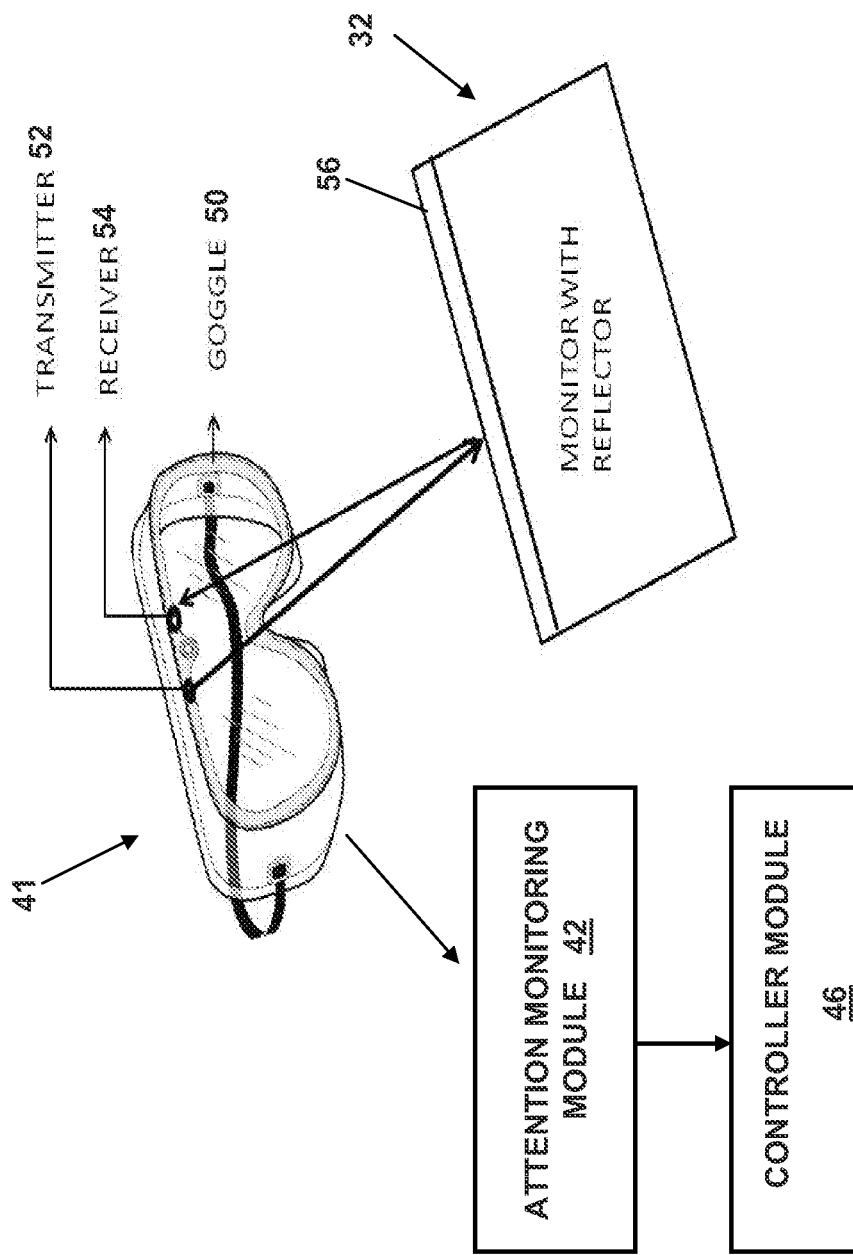
FIG. 3 illustrates an example of a gaze direction monitoring device that can be used with the radiation reduction and minimization apparatus.

FIG. 2 illustrates an embodiment of a radiation reduction and minimization apparatus 40 that can be connected to a radiation generation apparatus 24 in order to reduce/minimize unattended radiation of the radiation generation apparatus 24. The apparatus 40 may be implemented as a combination of hardware elements and software elements that perform the functions and operations described below. In other implementations, the apparatus may be implemented entirely in hardware (a specially programmed hardware device or the like). The apparatus 40 may comprise an attention monitoring module/unit 42 that receives inputs from one or more operator attention monitoring systems 41, that may be implemented using a head and/or brain sensing system, an eye or eyes sensing system or a gaze sensing system that are described below, and generates an attention (e.g., gaze focus) demand signal. The attention demand signal indicates that whoever in operating the radiation generating apparatus 24 has his/her attention appropriately focused, such as directed at/towards the monitor. In more detail, the attention monitoring module/unit 42 and controller 46 monitors all the users/operators to determine if and when the information generated by radiation is or may be used (e.g., the users/operators read the monitor information) and attention signal is generated. The attention demand signal is fed into a controller module/unit 46.

The operator attention monitoring systems 41 may alternatively include an image analysis and automated identification of a region of interest system. For example, the system can automatically identify the location of a tip of a catheter using well-known image processing techniques (for example identifying the motion of the device that is inside the body, a predetermined geometric shape of the device and/or a specially marked device) and the direction of the radiation towards this location in order to identify that the operator is alert since the catheter should be at the same location as the radiation. This may be accomplished in several ways including a built in software which performs proper image segmentation and object (say tool/catheter) recognition, followed by reference/access to a pre-loaded medical procedure knowledge (data) base, which will provide the coordinate for the focused radiation (region of high interest). This image analysis and automated identification of a region of interest system can be used with the other attention monitoring systems described above or can be used instead of the attention monitoring systems described above.

The apparatus 40 further may comprise a radiation activation module/unit 44 that receives inputs from one or more radiation activation devices 43, such as the radiation activator 34 in FIG. 1 or any other device that indicate an intent by the operator/assistant to activate the radiation source, and generates a radiation demand signal. The radiation demand signal indicates that the operator has activated the radiation activation devices (indicating intent by the operator/user to initiate radiation) indicating that radiation should be generated. The radiation activation devices may implemented in a variety of ways including a pedal (as shown in FIG. 1), a mechanical switch; a voice command, an optical designation as well as many others that are all can be used with the radiation minimization apparatus since the radiation minimization apparatus is not limited to any particular radiation activation devices. If the radiation activated device has been activated, the radiation demand signal is also fed into the controller module/unit 46.

The controller module/unit 46, based on the radiation demand signal and attention demand signal inputs, activates the radiation generating apparatus in such a way as to reduce/minimize unattended radiation. In particular, the radiation demand signal and the attention demand signal must indicate that the operator's attention is appropriately focused and that the radiation activation device has been activated by the operator. Since both signals must be present in order to activate the radiation generation apparatus, unattended radiation exposure is reduced/minimized. In particular, when the radiation activation device is activated, but the operator's attention is not appropriately focused (based on brain activity monitor and/or detection of the optical focusing by the eye tracking device), it is likely that the operator is not paying attention so no or minimal level (to be determined by the user) radiation is generated by the radiation generation apparatus. Similarly, if the operator's attention is appropriately focused, but the radiation activation device is not activated, the operator likely does not want radiation to be generated so no radiation is generated by the radiation generation apparatus. Thus, the controller module/unit 46 only enables the onset of radiation (using appropriate handshaking and control interface) when both the attention monitoring module and the radiation activation module send an ON signal.

The controller module/unit 46 may also control other aspects of the diagnostic/treatment system. In particular, the controller module/unit 46 may control the patient table 22 based on the attention of the operator. In typical system, most of the time a physician would like to have the center of his attention in the middle/center of the screen/monitor and the physician frequently manually repositions the table and the x-ray tube to achieve it in a typical system. Using the system described herein, the physician, when he/she decided that he/she wants to reposition the table, he/she sends command to the system to adjust table/x-ray tube position to their attention (for example based on their gaze location) and the system can automatically adjust the table. The physician command can be executed by either voice or switch. The operator will have an over-ride switch to turn this option on or off.

When radiation is to be generated by the radiation generation apparatus 24, the controller module/unit 46 may generate one or more radiation control parameters that are used to control the generation of the radiation by the radiation generation apparatus 24. The one or radiation control parameters may include a location of the radiation (when it is desirable to narrowly focus the radiation on a particular location), filtering and/or collimating (blocking) the radiation outside of the focus of attention, timing (the time that the radiation will be generated), frequency (the number of times over a predetermined amount of time that a pulsed radiation beam is generated) and intensity (for radiation generating apparatus in which the intensity of the radiation beam may be adjusted). For example, for an xray, kVP as the energy of the beam is used and mA-density for the intensity of the beam. The parameters may also include the amount of collimation/filtering of the radiation to restrict the beam to the point of attention. Other parameters of importance are the spatial and temporal rates of reduction from the center point with high radiation towards the periphery of the image where smaller (or no) level of radiation may be required.

In configurations with multiple radiation sources aimed at the same target (patient/object), the radiation parameters may also include an identifier of the radiation source to be used (sometimes at different times). Using these one or more radiation control parameters, the controller module/unit 46 can further minimize unnecessary radiation by ensuring that only the necessary amount of radiation for the particular task is used by controlling elements of the radiation generation apparatus such as the electronic grid, filtering, collimation, etc. The one or more radiation control parameters also can be used to ensure that radiation is only directed at a particular location when a particular location can be identified which reduces extraneous radiation on locations that do not need to be irradiated. In addition, the unattended radiation can be blocked using an electrical grid of the radiation source or by placing a shield that blocks the radiation. Now, several examples of situations in which unattended radiation can occur are described, including: 1) a "if you cannot use it, do not ask for it" situation; 2) a "where you see if where you get it" situation; and 3) "if you really want it, you will get it" situation.

"If you cannot use it—do not ask for it" Situation

During some phases of human visual processing, there are phases or time segments, such as the saccades (physiological eyes movements which occurs several times every second and last about 80 Millisecond each, or during "Perclose" (times when the eye lids are temporarily closed) where the brain doesn't acquire/process/exploit the visual information "landing" on the retinae (saccade masking) and useful visual information is only extracted during eye fixations phases. In this situation, a radiation minimization apparatus is used that has an operator saccade detector (the attention monitoring device 41 in this situation) synchronized with a radiation activation device). The radiation minimization apparatus turns off the radiation source during such "wasteful" time segments (such as "saccade masking"). One popular way to deliver the radiation is what is called "pulsed fluoroscopy" in which a pulse rate of 30 pulses per second is used. Using the radiation minimization apparatus, the pulses that are fall within the "wasteful" time segments (saccade masking and perclose) will be blocked.

In this situation, the attention/eye tracking monitoring devices 41 detects the phase of the operator visual path and, during the "inattentive" phases of the visual cycle, this module sends of signal to the controller module to block the radiation. The attention monitoring devices 41 may be implemented in several different ways. The first implementation may be gaze/eye tracking technology as described above. In another implementation, the attention monitoring devices 41 may be eyeball tracking technology (with three examples shown in FIG. 4A-4C). As shown in FIGS. 4A-4C, the eyeball tracking technology may be head or headband mounted version 400, a goggle mounted version 402 or a remote version 404 in which one or more sensors 406 (such as piezoelectric, magnetic, capacitive, IR, video or laser sensors, for example) are mounted to detect the eye movement of the operator. In specific implementations, the eyeball tracking technology may be an infrared cameras located in the radiation protection goggles, one or more capacity sensors located in the radiation protection goggles, one or more optical cameras located in the radiation protection goggles, laser emitter-receiver combination or Us sensors.

In this situation, the radiation activation module/unit 44 has the same elements and operation as described above in FIG. 2. The controller module/unit 46 also has the same elements and operation as described above in FIG. 2. In this situation, the apparatus prevents radiation exposure when the operator is not appropriately focused or looking at/towards the monitor 32.

"Where You See It Is Where You Get It" Situation

Figure 5A:
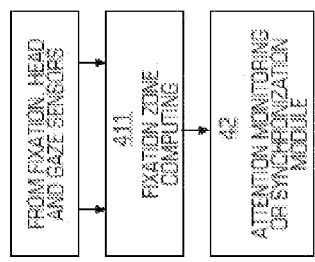
FIG. 5A-5B illustrates a fixation zone tracking implementation of the radiation reduction and minimization apparatus.
Figure 5B:
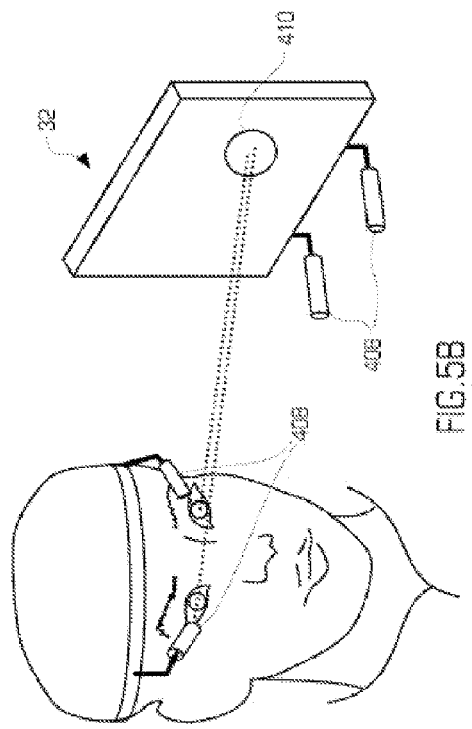

In many online procedures involving visual monitoring, most of the time the fixation zone of the operator is engaged with procedure details (e.g., a device, tool edge, anatomic feature etc.) of dimensions/sizes which are usually a small fraction (e.g., 1 to 5%) of the full imaged area (field of view (FOV)) [16 inch]. The image data surrounding this fixation zone, although useful for contextual information do not require the same refresh rate (frequency of radiation) nor the intensity and resolution needed within the fixation zone. Furthermore, even if provided, the operator doesn't fully perceive nor exploits the information outside this area of the highest visual and mental concentration (the fixation zone). In this situation, in order to reduce the radiation dose, the radiation is optimized by optimizing the radiation parameters (frequency, intensity, temporal and spatial resolutions) for each zone of the FOV on the basis of the utility of the information. An optimization process in the controller module 46 computes the proper parameters for each image segment. For example, in a simplistic embodiment of the process, the fixation zone receives high radiation frequency and high intensity of radiation and all other zones (background image) receive minimal (low) radiation or even no radiation, deploying past history images and avoid refresh altogether. In this situation, an operator fixation zone monitor is synchronized (via controller module) with a radiation activation device. As shown in FIGS. 5A and 5B, in this situation, the fixation sensors 408 are used to determine a fixation zone 410 of the operator on the monitor 32. The fixation sensors 408 operate is the same manner as the eye tracking since the eye tracking is based on the recording of the movement and location of the pupils that gives both gaze direction, eye movement and gaze/attention location. In this situation, the attention monitoring module includes a fixation zone determining module 411 that determine the fixation zone of the operator. In this situation, the attention monitoring devices may use similar attention monitoring devices as described above.

Figure 6A:
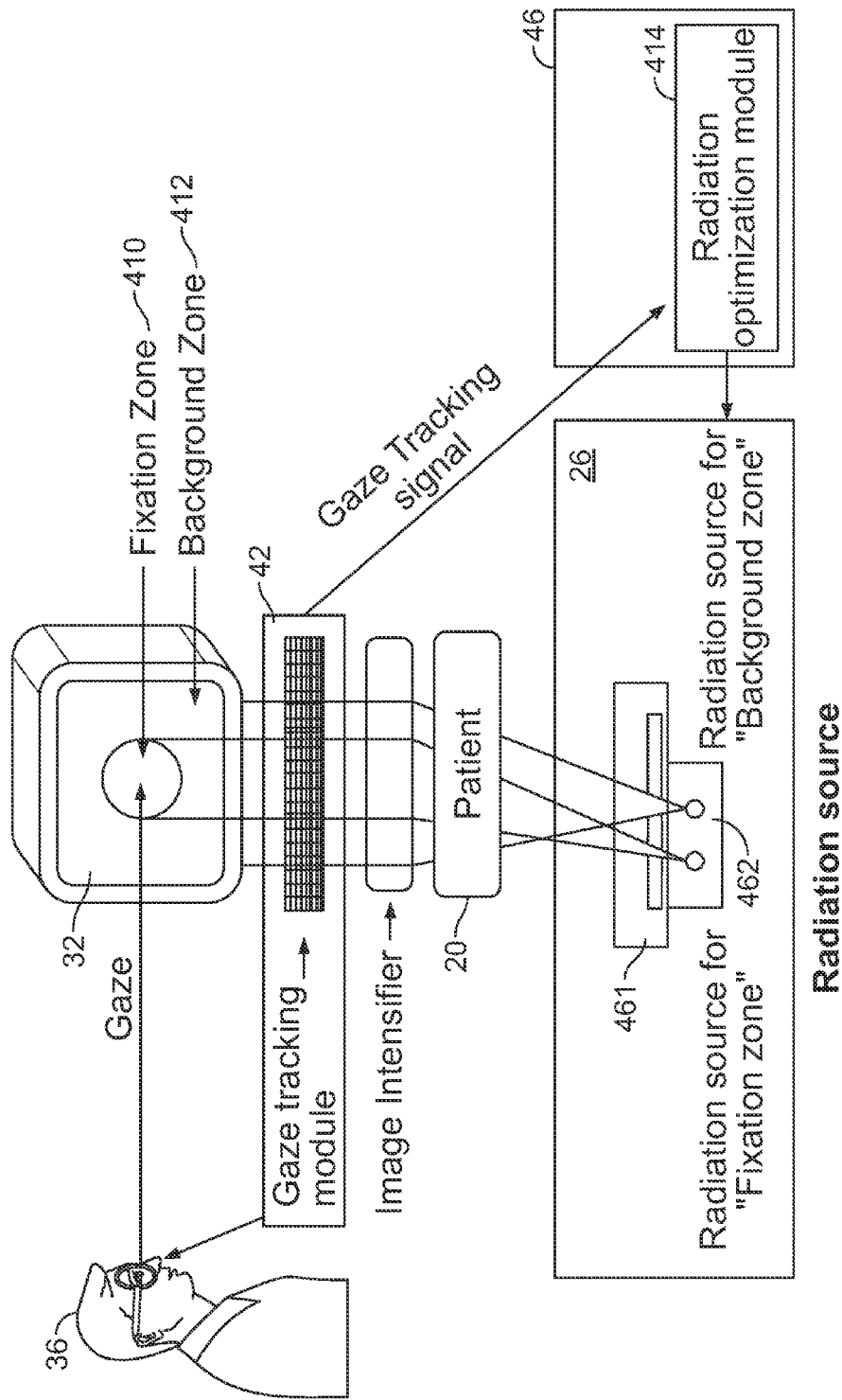
FIGS. 6A-6D illustrate different embodiments for controlling the radiation source when fixation zone tracking is used.
Figure 6B:
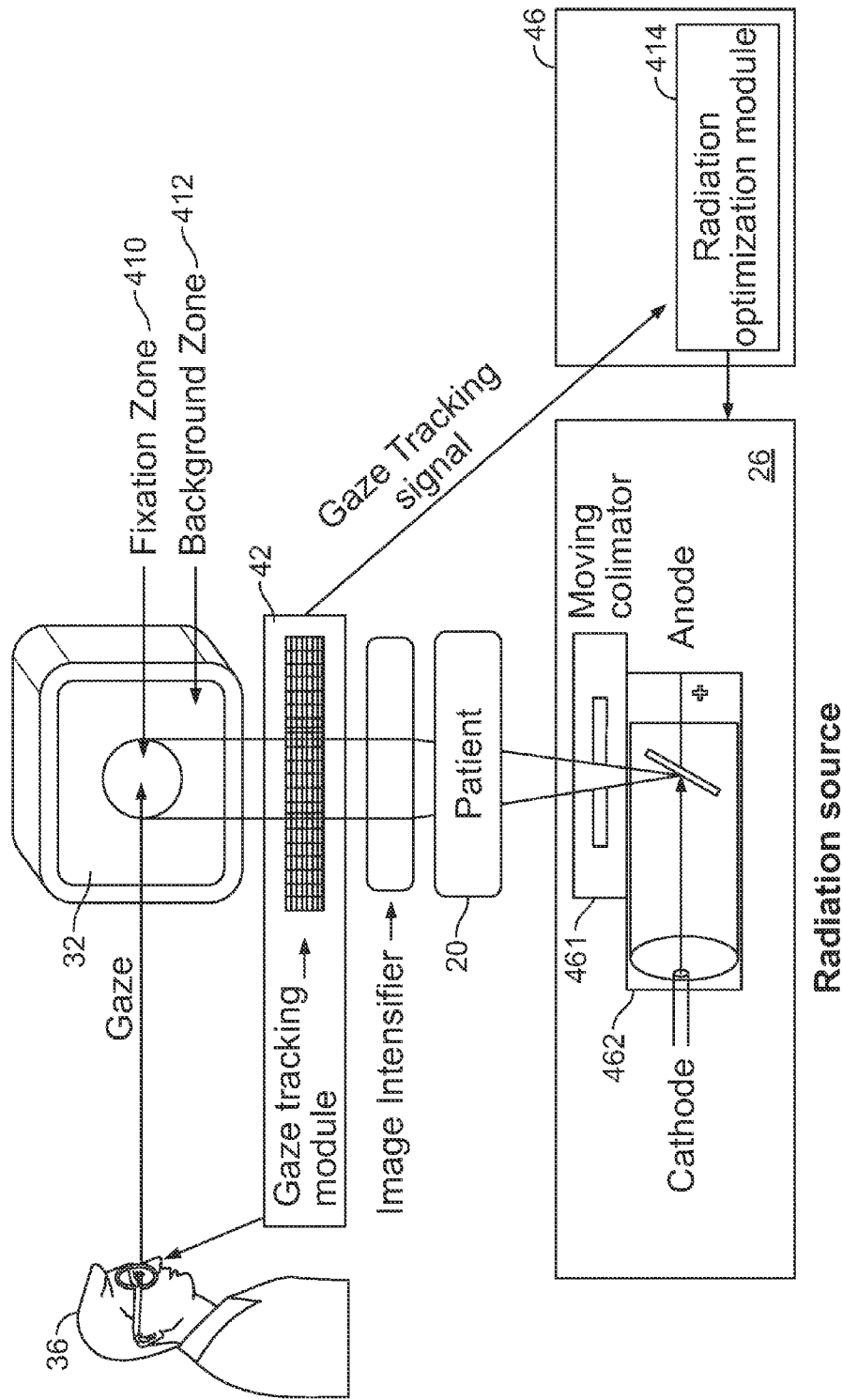
Figure 6C:
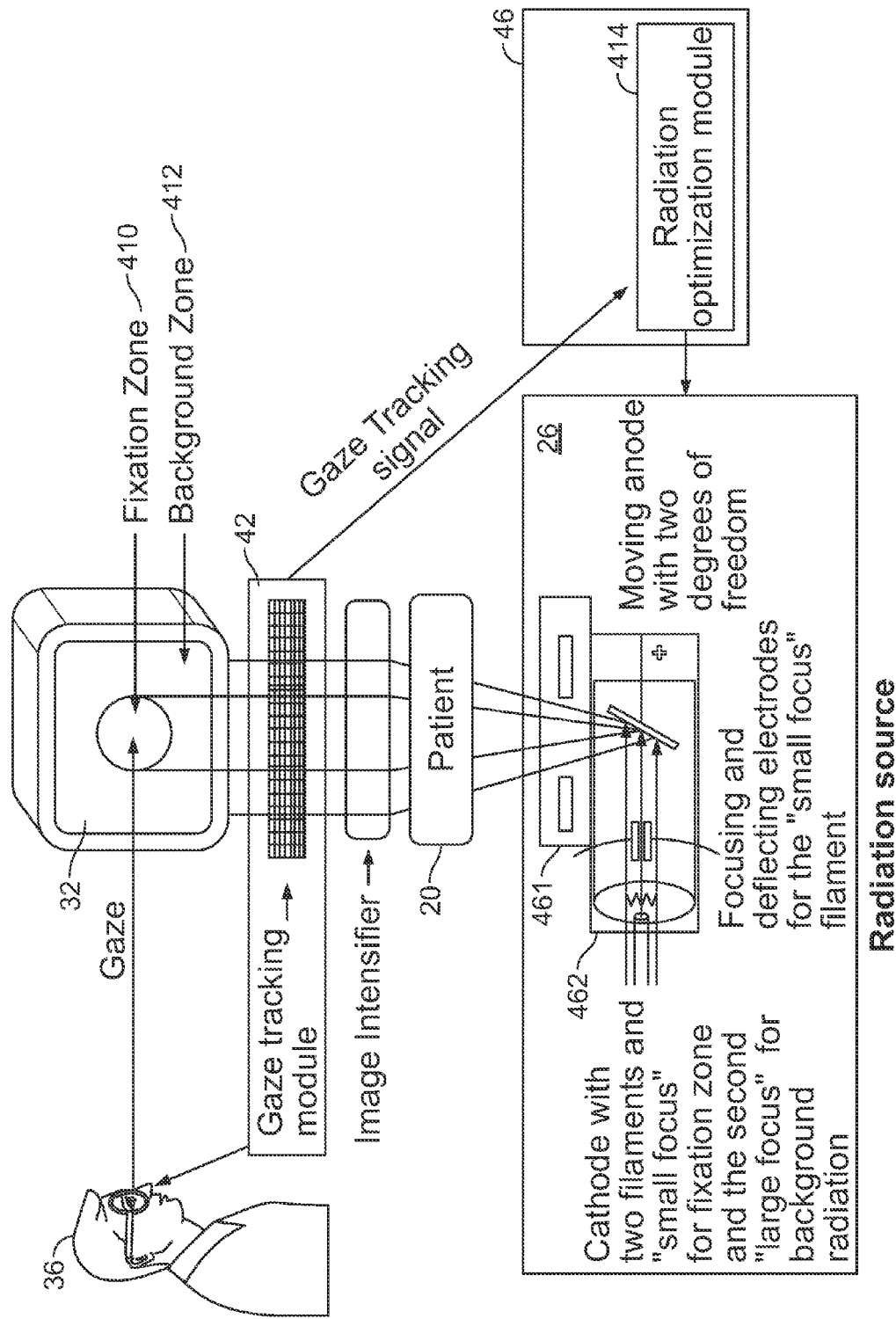
Figure 6D:
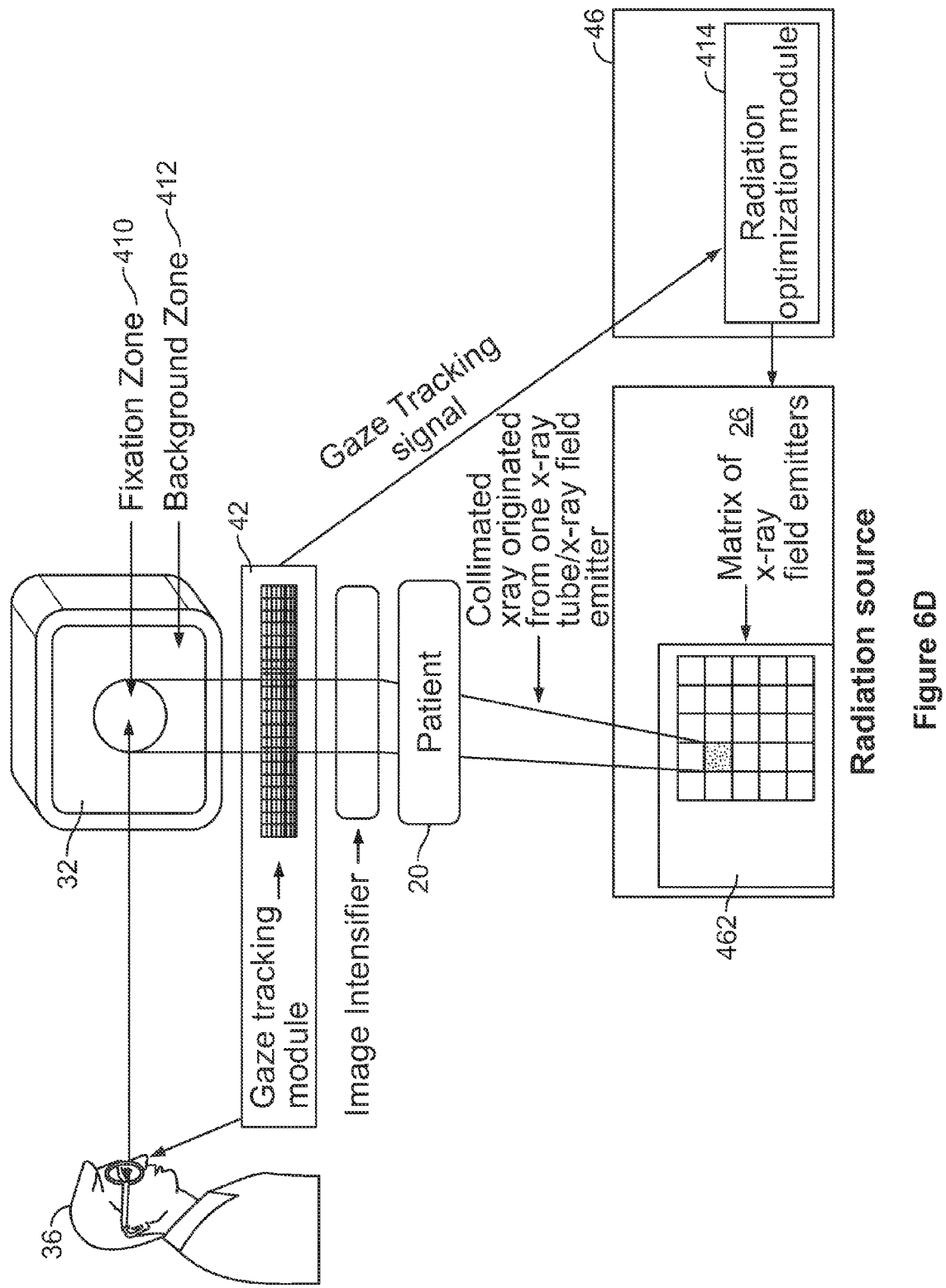

In this situation, the radiation activation module/unit 44 has the same elements and operation as described above in FIG. 2. For the controller module/unit 46 and the radiation source 26, several different embodiments are shown in FIGS. 6A-6C.

Figure 7:
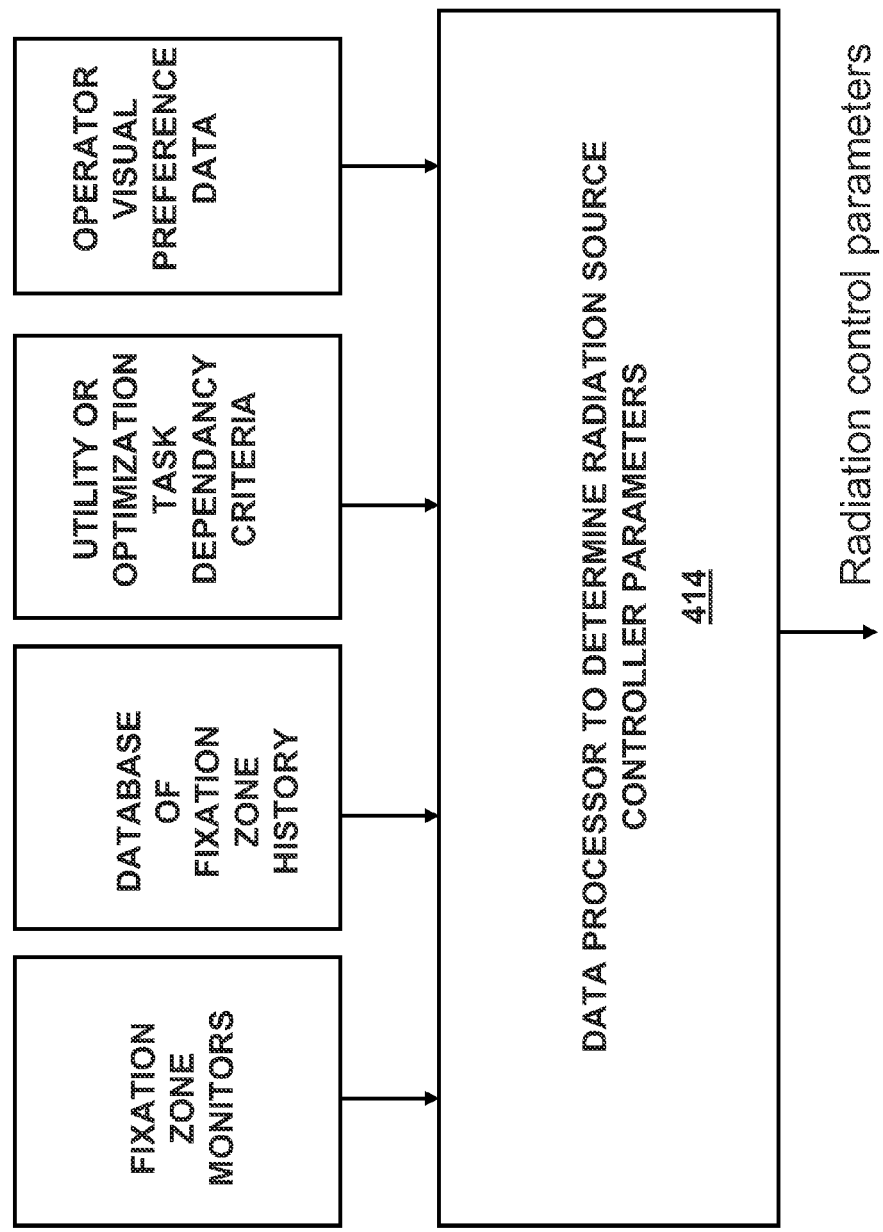
FIG. 7 illustrates more details of the controller module for fixation zone tracking.

The controller module 46 has a radiation optimization module 414 in each of the embodiments. The radiation optimization module 414 computes in real time (using the gaze tracking signal) and delivers to the radiation source controller, the optimal radiation parameters (pulse rate, intensity (mAm), energy (Kvp) of the radiation beam and resolution needed per each image segment within the entire FOV). This module may be using an optimization process which is using the archived history of fixation zones and their timing as tracked by the eyes as well as the radiated profiles and their timing as delivered for each image zone as shown in more detail in FIG. 7. The module allocates the minimal dosage necessary within each (pixel) image segment subset which is needed in order to deliver the necessary image clarity and validity (timing) to the operator. For example it will initially receive the information regarding the area of maximal attention of the FOV (the gaze tracking signal) from the attention monitoring module 42 as shown in FIG. 6A-6C. This area will be designated by the radiation optimization module 414 to receive significantly more radiation in terms of increased mAm and pulse rate than the rest of FOV in order to provide optimal imaging. This will result in much better temporal, contrast and spatial resolution that in term will improve the operator performance. The radiation profile and radiation parameters are then transferred the radiation source 26.

The radiation source 26, for this situation, is designed so that the radiation source can deliver different radiation doses to the different segments of the FOV. This may be carried out by the controller module that generates a collimator control signal to adjust the collimators that adjust the radiation dosage of the radiation beam. The collimator control signal may be continuously adjusted so that, consequently, the radiation dose of the radiation source towards a portions of the patient is adaptively adjusted and controlled. Generally, this can be achieved using either mechanical or electronic collimators, electron beam radiation source or combination of several radiation sources. In one implementation, the radiation source 26 may be a standard radiation source, such as an x-ray tube, with moving mechanical collimator or region of interest (ROI) filter so that the mechanical collimators(or filters) 461 as shown in FIG. 6A can be used dynamically expose the areas of maximal attention 410 and collimate the rest areas of FOV 412. In another implementation, two or more radiation sources 462, such as an x-ray tubes, as shown in FIG. 6A may be used in which the several radiation sources provide the radiation for the area of maximal attention and the others for the rest of FOV with corresponding collimators arrangements. In yet another implementation of the radiation source, the radiation source may have a anode/cathode 462 as shown in FIG. 6B and a moving collimator (or ROI filter) 461 that is used to adjust the radiation directed towards the fixation zone 410 and towards the background zone 412.

In yet another implementation, the radiation source may have a collimator (or ROI filter) 461 and a anode with a complex geometry 462. In this implementation, the radiation source are designed the way similar to the Electron beam CT (see for example U.S. Pat. No. 4,352,021) in which the electrons that originate at the cathode are directed by an external magnetic field toward different segments/parts of the anode or to the different anode targets. The anode is designed as a complex array of geometrically oriented targets (for example, a matrix of the targets). The anode also can be mechanically moved in order to change the angle and thus create an additional option for moving the radiation beam. The application/direction of the electron beam to the different parts of the anode result in the change in the direction of the radiation. The direction of the radiation will then correlate with the area of maximal attention. The radiation of the rest FOV will be provided either by different xray tube or different electron beam source in the same x ray tube.

In yet another implementation, the radiation source may have matrix of radiation field emitters 462 (or small conventional radiation tubes that are commercially available.) The electron field emission are attractive way to extract free electrons because the electrons are emitted at room temperature and the output current is voltage controllable. Recently the researchers from the UNC optimized the morphology of carbon nanotubes (CNT) films that optimize the electrons current for the xray generators (See U.S. Pat. No. 7,085,351 b2). In this scenario the non uniform radiation can be activated (or the changing of the radiation parameters) using different combination of the radiation field emitters. The x-rays that are generated using CNT are high frequency and high intensity and more programmable. The xray source can be designed as a square matrix of the multiple field emission xray tubes or conventional radiation tubes. In this design the each xray tube is separately programmable and can deliver the xray beam of desired intensity to the specific area. For example one of the xray tubes will deliver the maximum radiation dose to the maximum attention area 410 and the others deliver lower radiation dose to the rest of the field of view 412.

The matrix of radiation, such as x-ray, tubes also can be extended to resemble a partial CT scanner. In this case, it is possible to create a 3D or CT type of images and the generation of CT images during fluoroscopy guided interventional procedures is a very desirable feature for the surgeon. However, the continuous CT type of scanning of the whole body subjects the patient to a large amount of radiation. Using the radiation minimization and reduction apparatus above with the attention monitoring, the CT type of scanning of the whole body can be performed in the specific fixation zones 410 and the images are intermittently generated so that the radiation exposure is reduced.

"If You Really Want It, You Will Get It" Situation

In many situations an operator may be looking, even fixating steadily at an image subzone—yet his/her "mind" drifts off "thinking/engaging" in mental activities which are not directly related to the task at hand. Brain monitoring technology 800 may be used which when deployed will allow for setting off an alert signal whenever the operator switches his/her attention/focus from the current task. In this situation, the operator attention focusing/brain state monitor 800 and the fixation zone monitor 42 are synchronized as shown in FIG. 8.

Figure 8:
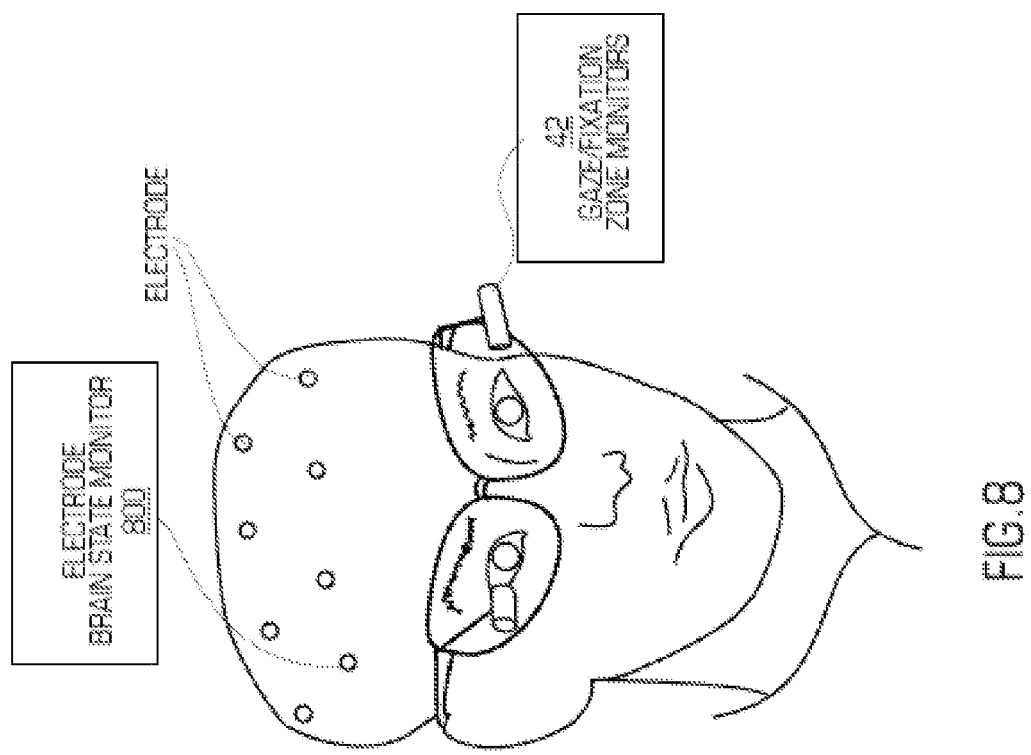
FIG. 8 illustrates a brain activity monitoring implementation of the radiation reduction and minimization apparatus.

The mental attention monitoring module 800 may be a module, such as the electrodes and the brain state monitor shown in FIG. 8, so that mental attention can be monitored using the ECG electrodes (see for example, U.S. patent application Ser. No. 11/145,612 that lists Bruce Katz and Allon Guez as inventors that is titled "Brain State Recordation System", the entirety of which is incorporated herein by reference. In this situation, the radiation activation module and controller module have the same elements and operation as described herein.

While the foregoing has been with reference to a particular embodiment of the invention, it will be appreciated by those skilled in the art that changes in this embodiment may be made without departing from the principles and spirit of the disclosure, the scope of which is defined by the appended claims.

The invention claimed is:

1. A radiation device, comprising:
  a radiation source that generates a radiation beam that is directable towards a subject;
  a radiation controller connected to the radiation source, the radiation controller having a fixation zone module that determines a fixation zone of an operator of the radiation source and the radiation controller generates a collimator control signal based in part on the determined fixation zone of the operator; and
  a collimator, connected to the radiation controller, that based on the collimator control signal, continually filters the radiation that is outside of a region of interest to reduce a radiation dose from the radiation source for radiation that is outside of the region of interest.

2. The device of claim 1, wherein the radiation source has an movable anode that is mechanically moved to move the radiation beam.

3. The device of claim 2, wherein the movable anode changes a direction of the radiation beam.

4. The device of claim 1, wherein the radiation source has a matrix of radiation emitters.

5. The device of claim 4, wherein the matrix of radiation emitters further comprises a square matrix of multiple field emission x-ray tubes and each field emission x-ray tube is separately programmable to direct a radiation dose towards a particular area.

6. The device of claim 5, wherein the matrix of radiation emitters further comprises a square matrix of multiple radiation tubes and each radiation tube is separately programmable to direct a radiation dose towards a particular area.

7. The device of claim 6, wherein a first field emission x-ray tube directs a maximum radiation dose to an area of maximum attention and a second field emission x-ray tube directs a lower radiation dose to a field of view that does not include the area of maximum attention.

8. The device of claim 7, wherein a first radiation tube directs a maximum radiation dose to an area of maximum attention and a second radiation tube directs a lower radiation dose to a field of view that does not include the area of maximum attention.

9. A radiation minimization method, comprising:
generating, using a radiation source, a radiation beam that is directable towards a subject;
determining, by a fixation zone module of a radiation controller, a fixation zone of an operator of the radiation source;
generating, by the radiation controller, a collimator control signal based in part on the determined fixation zone of the operator; and
filtering, by a collimator connected to the radiation controller based on the collimator control signal, the radiation that is outside of a region of interest to reduce a radiation dose from the radiation source for radiation that is outside of the region of interest.

10. The method of claim 9 further comprising mechanically moving an anode of the radiation beam to move the radiation beam.

11. The method of claim 10, wherein mechanically moving the anode further comprises changing a direction of the radiation beam.

12. The method of claim 9, wherein generating the radiation beam further comprises directing, by a square matrix of multiple field emission x-ray tubes, a radiation dose by each field emission x-ray tube to a particular area.

13. The method of claim 9, wherein generating the radiation beam further comprises directing, by a square matrix of radiation tube, a radiation dose by each radiation tube to a particular area.

14. The method of claim 12, wherein directing the radiation dose further comprises directing, by a first field emission x-ray tube, a maximum radiation dose to an area of maximum attention and directing, by a second field emission x-ray tube, a lower radiation dose to a field of view that does not include the area of maximum attention.

15. The method of claim 13, wherein directing the radiation dose further comprises directing, by a first radiation tube, a maximum radiation dose to an area of maximum attention and directing, by a second radiation tube, a lower radiation dose to a field of view that does not include the area of maximum attention.

* * * * *

UNITED STATES PATENT AND TRADEMARK OFFICE
CERTIFICATE OF CORRECTION

PATENT NO. : 8,754,388 B2
APPLICATION NO. : 13/856429
DATED : June 17, 2014
INVENTOR(S) : Allon Guez It is certified that error appears in the above-identified patent and that said Letters Patent is hereby corrected as shown below:

In the Claims:

At column 9, claim number 2, line number 4, replace "an" with --a--.

At column 9, claim number 6, line number 15, replace "claim 5" with --claim 4--.

At column 9, claim number 7, line number 19, replace "claim 6" with --claim 5--.

At column 9, claim number 8, line number 24, replace "claim 7" with --claim 6--.

At column 10, claim number 13, line number 21, replace "tube" with --tubes--.

Signed and Sealed this
Seventh Day of October, 2014

Michelle K. Lee
*Deputy Director of the United States Patent and Trademark Office*